United States Patent
Lowin (10) Patent No.: US 11,052,262 B1
(45) Date of Patent: Jul. 6, 2021

(54) STIMULATION OF SUBCORTICAL BRAIN REGIONS USING TRANSCRANIAL ROTATING PERMANENT MAGNETIC STIMULATION (TRPMS)

(71) Applicant: Seraya Medical Systems LLC, Greenwich, CT (US)

(72) Inventor: Leeam Lowin, Greenwich, CT (US)

(73) Assignee: SERAYA MEDICAL SYSTEMS LLC, Greenwich, CT (US)

( * ) Notice: Subject to any disclaimer, the term of this patent is extended or adjusted under 35 U.S.C. 154(b) by 0 days.

(21) Appl. No.: 16/730,266

(22) Filed: Dec. 30, 2019

(51) Int. Cl.
*A61N 2/12* (2006.01)

(52) U.S. Cl.
CPC ..................... *A61N 2/12* (2013.01)

(58) Field of Classification Search
CPC .. A61N 2/12; A61N 2/006; A42B 1/04; A42B 1/242; A61B 5/0476; A61B 5/05; A61B 5/6803
USPC ....................................... 600/9–15
See application file for complete search history.

(56) References Cited

U.S. PATENT DOCUMENTS

| | | | |
|---|---|---|---|
| 6,488,617 B1 * | 12/2002 | Katz | A61B 5/0482 600/26 |
| 8,958,882 B1 * | 2/2015 | Hagedorn | A61N 1/36025 607/45 |
| 9,456,784 B2 | 10/2016 | Helekar | |
| 9,782,602 B1 * | 10/2017 | Lowin | G01K 13/00 |
| 2009/0099623 A1 * | 4/2009 | Bentwich | A61N 5/0613 607/45 |
| 2010/0113959 A1 * | 5/2010 | Pascual-Leone | A61N 2/008 600/544 |
| 2010/0256438 A1 * | 10/2010 | Mishelevich | A61N 2/006 600/13 |

(Continued)

OTHER PUBLICATIONS

Swanson, K.D., Lok, E. & Wong, E.T. An Overview of Alternating Electric Fields Therapy (NovoTTF Therapy) for the Treatment of Malignant Glioma. Curr Neurol Neurosci Rep 16, 8 (2016). (Year: 2016).*

(Continued)

*Primary Examiner* — Navin Natnithithadha
*Assistant Examiner* — Sunita Reddy
(74) *Attorney, Agent, or Firm* — Leason Ellis LLP (57) ABSTRACT

A method of affecting a biological, cellular or biochemical function or structure in a targeted subcortical location in a brain of a patient using a TRPMS apparatus placed on a head of the patient includes positioning two or more of a plurality of magnetic assemblies on locations of the head mount selected to stimulate the targeted subcortical location in the brain of the patient, and activating the plurality of magnetic assemblies at the selected locations to generate magnetic fluxes of a selected strength, frequency and duration directed into the brain of the patient, wherein the magnetic flux directed into the brain of the patient from each of the assemblies is operative to generate induced electric field in regions of the brain and the regions of induced electric fields generated by each of the plurality of magnetic assemblies converge in the targeted subcortical location and combine to a magnitude sufficient to affect the biological, cellular or biochemical function or structure in the targeted subcortical location.

15 Claims, 8 Drawing Sheets

(56) References Cited

U.S. PATENT DOCUMENTS

| | | | | |
|---|---|---|---|---|
| 2012/0157752 A1* | 6/2012 | Nishikawa | A61N 2/006 | 600/15 |
| 2013/0137918 A1* | 5/2013 | Phillips | A61B 2/02 | 600/14 |
| 2013/0338424 A1* | 12/2013 | Pascual-Leone | A61N 2/006 | 600/13 |
| 2014/0276182 A1* | 9/2014 | Helekar | A61B 5/04008 | 600/544 |
| 2015/0038768 A1* | 2/2015 | Saitoh | A61N 2/006 | 600/13 |
| 2016/0008620 A1* | 1/2016 | Stubbeman | A61N 1/36082 | 600/14 |
| 2016/0015588 A1* | 1/2016 | Tamiya | A61G 15/125 | 128/845 |
| 2016/0193476 A1* | 7/2016 | Helekar | A61B 5/05 | 600/544 |
| 2017/0136255 A1* | 5/2017 | Helekar | A61B 5/0036 | |
| 2017/0368366 A1* | 12/2017 | Lowin | A61N 2/12 | |
| 2018/0071545 A1* | 3/2018 | Saitoh | A61N 1/40 | |
| 2019/0247662 A1* | 8/2019 | Poltroak | A61B 5/04009 | |

OTHER PUBLICATIONS

Santini SJ, Cordone V, Falone S, et al. Role of Mitochondria in the Oxidative Stress Induced by Electromagnetic Fields: Focus on Reproductive Systems [published correction appears in Oxid Med Cell Longev. May 17, 2020;2020:5203105], Oxid Med Cell Longev. 2018:2018:5076271. Published Nov. 8, 2018. (Year: 2018).*

Helekar, S.A., et al., "Transcranial brain stimulation with rapidly spinning high-field permanent magnets", Article in IEEE Access—Jan. 2016, pp. 1-8.

Helekar, S.A., et al., "The strength and spread of the electric field induced by transcranial rotating permanent magnet stimulation in comparison with conventional transcranial magnetic stimulation", Journal of Neuroscience Methods, vol. 309, 2018, pp. 153-160.

Zaidi, Nur Syamimi, et al., "Magnetic Field Application and its Potential in Water and Wastewater Treatment Systems", Separation & Purification Reviews, vol. 43, 2014, pp. 206-240.

International Search Report and Written Opinion dated Mar. 17, 2021, corresponding to International Patent Application No. PCT/US2020/067489; 11 pages.

* cited by examiner

STIMULATION OF SUBCORTICAL BRAIN REGIONS USING TRANSCRANIAL ROTATING PERMANENT MAGNETIC STIMULATION (TRPMS)

FIELD OF THE INVENTION

The present invention relates to medical devices, and more particularly, relates to a system and method for neurostimulation of electrical or electrochemical activity in cortical or subcortical brain regions by application of convergent magnetic fields generated by a plurality of magnetic assemblies in a Transcranial Rotating Permanent Magnetic Stimulation (TRPMS) apparatus.

BACKGROUND OF THE INVENTION

Figure 1:
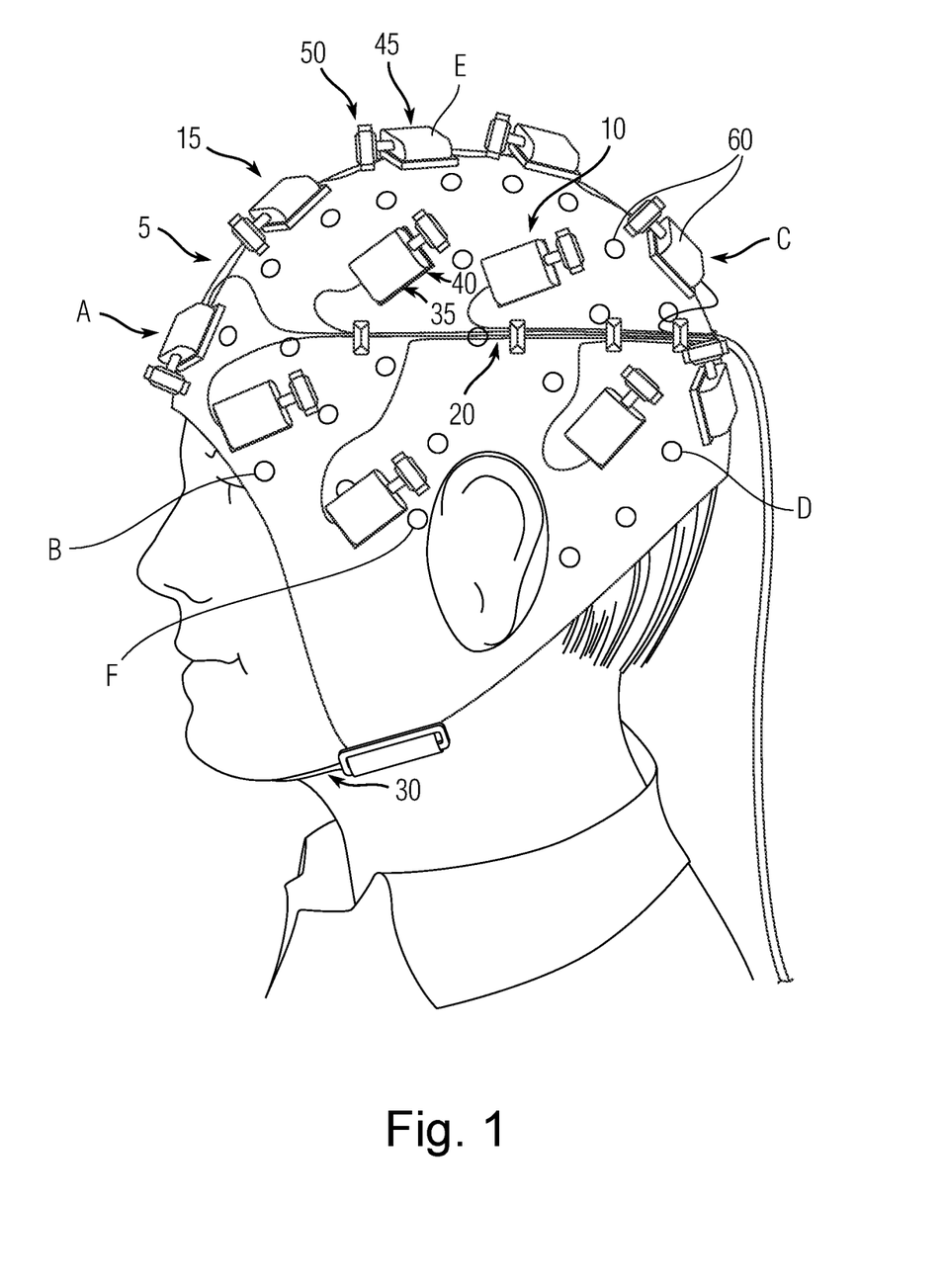
FIG. 1 is a side view of an example transcranial rotating permanent magnetic stimulation (TRPMS) apparatus that can be used in the context of the present invention.

Commonly-owned U.S. Pat. No. 9,456,784, entitled "Method and Apparatus for Providing Transcranial Magnetic Stimulation (TPMS) to a Patient" describes a transcranial rotating permanent magnetic stimulation apparatus ("TRPMS apparatus") that includes replaceable magnet assemblies that can be used to generate various patterns of transcranial magnetic stimulation. FIG. 1 is a side view of an example TRPMS apparatus 5. As shown, the TRPMS apparatus 5 includes a head mount or cap 10 for positioning on a subject's head and a plurality of magnet assemblies 15 that can be attached at specific attachment locations e.g. A, B, C, D, E, F to the surface of the head mount (in FIG. 1, magnetic assemblies are shown attached at locations A, C and E, obscuring the attachment points). The magnet assemblies are connected by leads 25 to a computer device (not shown in FIG. 1). The computer device can be programmed to activate any or all magnet assemblies to generate transcranial magnetic stimulation suited for a specific treatment. For example, the computer device can control magnets at different locations to deliver different magnitudes of stimulation, or to generate particular waveforms of stimulation (e.g., in periodic bursts or oscillatory waves) suited for stimulating activity in specific brain regions.

These waveforms are applied to the magnetic assemblies to set them into motion and to control rotation in order to deliver highly focal stimuli. The various parameters for controlling the magnetic assemblies, which include the waveforms (which can be applied in packet bursts), duty cycles, magnitudes, and rates of rotation, are tailored to the particular treatment or therapy contemplated. As such, the demands on the magnetic assemblies can vary depending on the intended treatment. Commercially available magnetic assemblies preferably are labeled as being approved for particular uses and for a finite number of times before being discarded.

Thus far, the magnetic assemblies using permanent magnets have been used for low-depth cortical stimulation. However, there are conditions for which shallow-depth stimulation does not produce therapeutic results. What is therefore needed is a system and method that provides stimulation of deeper areas of the brain for therapeutic, diagnostic and other purposes.

SUMMARY OF THE INVENTION

The present disclosure provides a method of stimulating or otherwise bioelectromagnetically affecting a biological, cellular or biochemical function or structure in a targeted subcortical location in a brain of a patient using a TRPMS apparatus provided on a head mount having a plurality of releasable magnetic assemblies with rotating permanent magnets operable to rotate for controlled durations and spin rates. The method comprises positioning two or more of the plurality of magnetic assemblies on locations of the head mount selected to affect the biological, cellular or biochemical function or structure at the targeted subcortical location in the brain of the patient, and activating the plurality of magnetic assemblies at the selected locations to generate magnetic fluxes of a selected strength, frequency and duration directed into the brain of the patient, wherein the magnetic flux directed into the brain of the patient from each of the assemblies is operative to generate induced electric field in regions of the brain. The regions of induced electric fields generated by each of the plurality of magnetic assemblies converge and overlap in the targeted subcortical location and combine to a magnitude sufficient (i.e., as strong as necessary) to stimulate neurons or to modulate biological, cellular and/or biochemical processes within brain structures in the targeted subcortical location. It is also noted that the strength of the induced electric fields in regions outside of the region of overlap is minimized to avoid unwanted stimulation of brain structures outside of the region in which the convergent filed overlap.

The present disclosure further provides an apparatus for stimulating or biomagnetically affecting a biological, cellular or biochemical function or structure in a targeted subcortical location in a brain of a patient. The apparatus comprises a head mount positioned on the patient, and a plurality of releasable magnetic assemblies coupled to the head mount including rotating permanent magnets operable to rotate for controlled durations and spin rates, the plurality of magnetic assemblies being selectively positioned at locations of the head mount to stimulate or affect the targeted subcortical location in the brain of the patient. Activation of each of the plurality of magnetic assemblies at the selected locations causes magnetic fluxes of a selected strength, frequency and duration to be directed into the brain of the patient, wherein the magnetic flux directed into the brain of the patient from each of the assemblies is operative to generate induced electric field in regions of the brain. The regions of induced electric fields generated by each of the plurality of magnetic assemblies converge and overlap in the targeted subcortical location and combine to a magnitude as strong as necessary to stimulate neurons or to modulate biological, cellular and/or biochemical processes within brain structures in the targeted subcortical location.

These and other aspects, features, and advantages can be appreciated from the following description of certain embodiments of the invention and the accompanying drawing figures and claims.

DETAILED DESCRIPTION OF CERTAIN EMBODIMENTS OF THE INVENTION

The following description discloses a TRPMS apparatus and method for stimulating or otherwise bioelectromagnetically affecting a biological, cellular or biochemical function or structure in a targeted cortical or subcortical brain regions using a plurality of magnetic assemblies mounted on the skull of a patient. The term "bioelectromagnetically" as used herein means pertaining to the interaction between an external magnetic field and biological tissues, structures and functions. The magnetic assemblies employ rotating permanent magnets to generate time-varying magnetic fields that induce electric currents at a targeted location in the brain of the patient. TRPMS has the advantage that the spatial spread of the magnetic field and induced current is more limited in comparison to related methods such as TMS, which employs electromagnetic coils. On the other hand, TRPMS suffers from the disadvantage that magnetic field strength tends to be lower than TMS. This disadvantage is overcome by employing multiple magnetic assemblies to generate magnetic fields that, at least in part, converge at the target location. By such convergence, the magnetic fields produced by the distinct assemblies combine according to the principle of superposition to boost the magnetic field strength to levels sufficient to achieve changes in the frequency of fasciculation potentials or spontaneous motor unit potentials (sMUPs) in localized cortical or subcortical regions. Additionally, in certain applications the magnetic field strength is applied at a level as strong as necessary to modulate biological, cellular and/or biochemical processes within brain structures.

Figure 2:
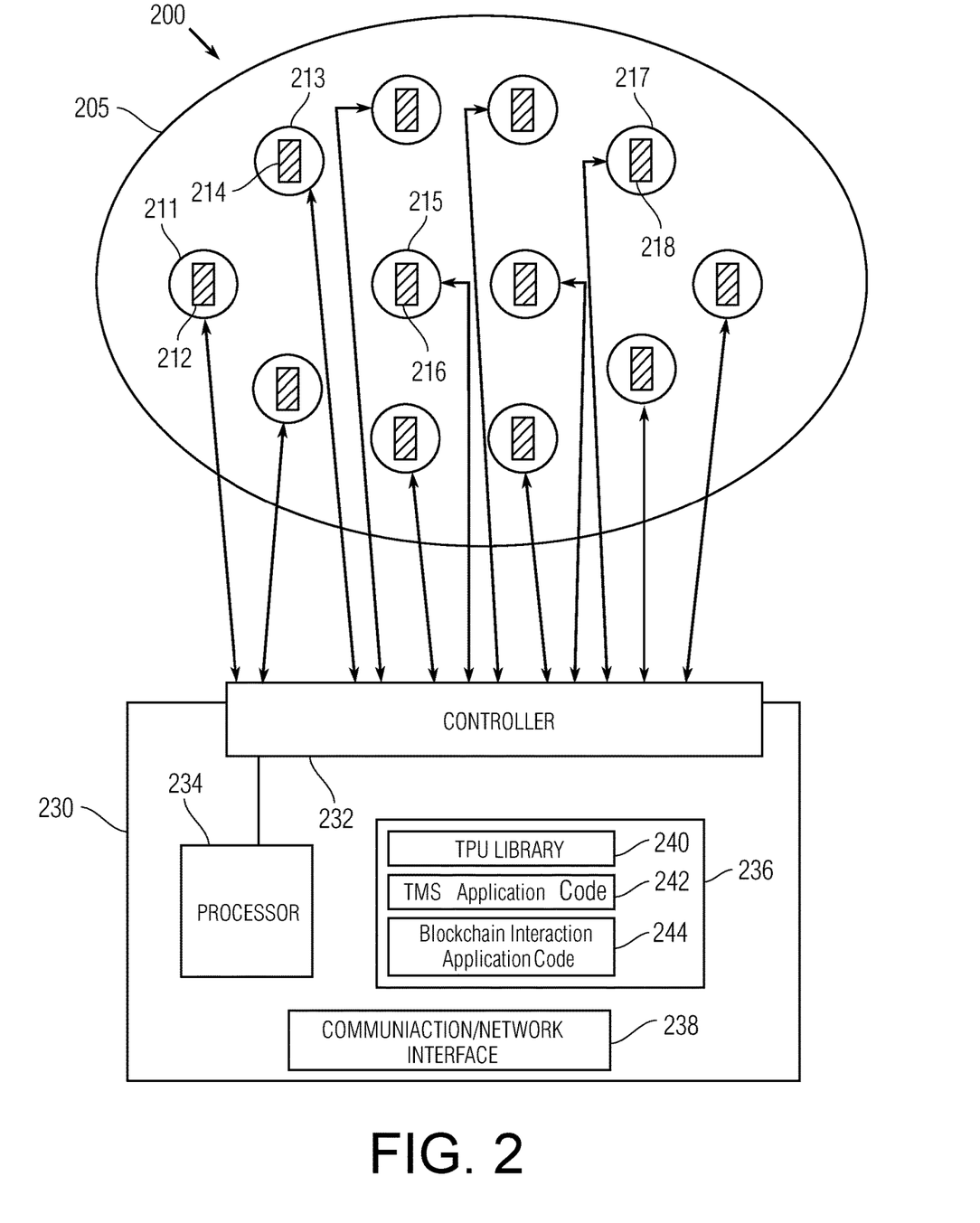
FIG. 2 is a schematic plan view of an example transcranial magnetic system that can be used in the context of the present invention.

The following sections discuss an exemplary embodiment of a TRPMS apparatus that can be used in the context of the methods disclosed herein. FIG. 2 is a schematic plan view of an example transcranial magnetic system 200. A harness, head mount or cap 205 ("head mount") is configured with a plurality of attachment points e.g., 211, 213, 215, 217 where one or more respective magnetic assembly devices 212, 214, 216, 218 can be detachably connected. In certain implementations, the magnetic assembly devices are connected to the head mount using hook or loop type fasters such as Velcro. The attachment points represent specific locations on the head mount and both the number of magnetic assembly devices used, and the positions at which they are deployed at the attachment point on the head mount, depend on the medical conditions (treatment) for which the TRPMS is applied. In some embodiments, the attachment points can be at predetermined positions on the head mount surface. The head mount can also be equipped with rails, channels or similar structures containing conductive elements that enable a given magnetic assembly device to be secured at variable points along the channel or rail, depending on the desired treatment location or the cranial structure of a given subject. In such an embodiment, a rheostat or equivalent circuit can be employed to electronically identify the variable location of a given magnetic assembly on the head mount 205. The attachment points can all be of like design to permit a standard magnetic assembly device to be attached anywhere along the head mount 205, or the attachment points can provide more than one fitting to only mate with corresponding magnetic assembly devices.

The attachment points, 211, 213, 215, 217 which correspond to regions on the cranium where magnetic fields are applied, are optimized for delivery of magnetic energy for a given diagnosis, therapy, mapping, or other application. The arrangement shown in FIG. 2 is exemplary and it will be appreciated that numerous other configurations can be employed depending on the intended application. The magnetic assembly devices are controlled (i.e., activated, driven and deactivated) by a control device 230 that includes a controller interface 232 ("controller") that is electrically coupled to each of the magnetic assembly devices 212, 214, 216, 218.

Figure 3A:
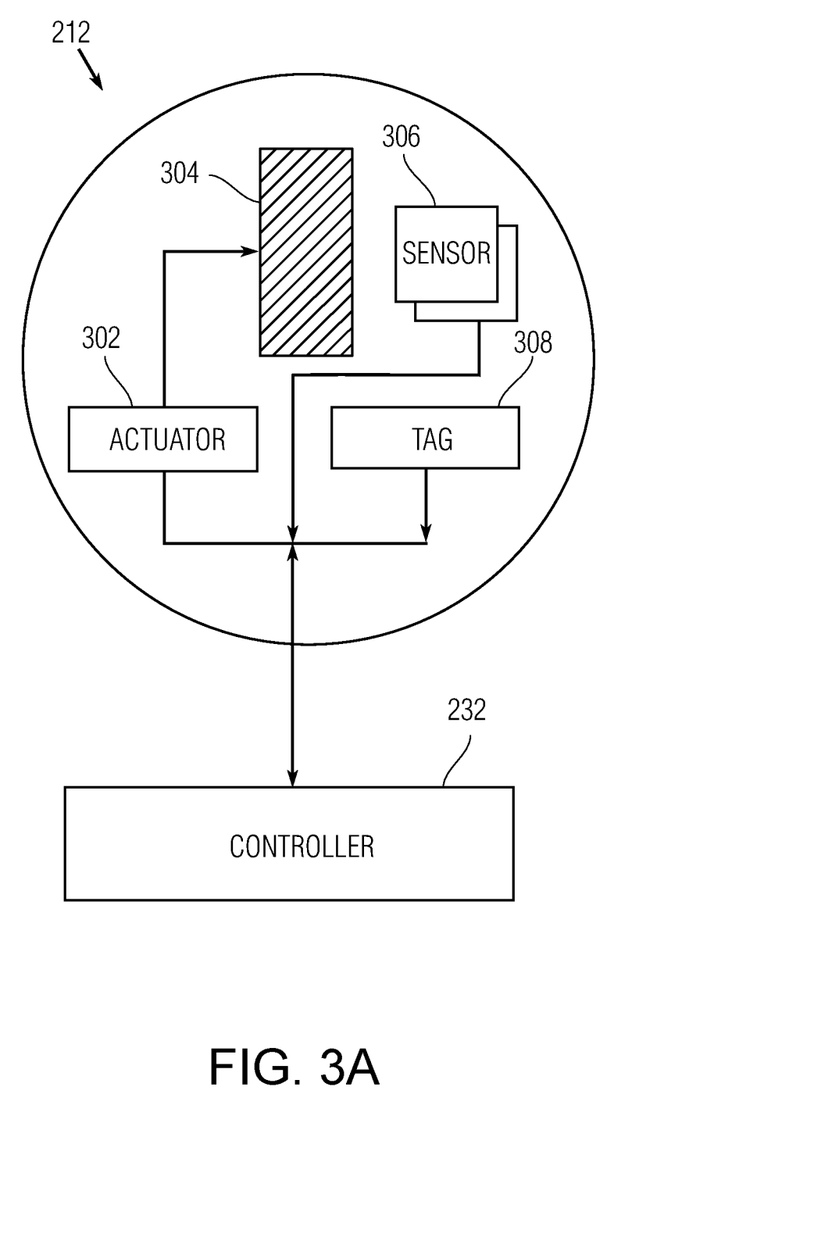
FIG. 3A presents a block diagram illustrating an exemplary magnetic assembly device.

FIG. 3A provides a more detailed illustration of an exemplary magnetic assembly device e.g., 212. The magnetic assembly device includes an actuator device 302 which can be implemented as a motor, such as a stepper or bushed motor that can run at variable speeds, for example, up to 24,000 revolutions per minute (RPM). Other actuator device types known to those of skill in the art can be utilized in certain embodiments. The actuator device 302 is electrically coupled to the controller 232 from which it receives electrical signals that drive the actuator device. The actuator device 302 is mechanically and rigidly coupled to a magnet 304, such as via a rotor shaft, and is arranged to cause the magnet 304 to rotate when driven by control signals from the controller 232.

In accordance with various embodiments, the magnet 304 can be implemented as a permanent magnet of a variety of different sizes and strengths. The permanent magnet 304 can be composed of a rare earth material such as neodymium. In an alternative arrangement, the magnet 304 can be implemented as a soft magnetic composite ("SMC") magnet. In certain implementations, the magnets can be cylindrical (¼ in. by ⅜ in.) axially magnetized neodymium magnets (N52 grade) manufactured by K&J Magnetics of Jamison, Pa.

Rotation of the magnet 304 creates a rapidly changing magnetic field. In some embodiments, each of the magnet assembly devices provide a rapidly changing magnetic field of at least 500-600 Tesla/second and a magnet movement speed of no less than 400 Hertz. As will be appreciated by those knowledgeable in the field of TRPMS, the changing magnetic field generated by the rotating permanent magnets induces electric fields within the brain of the patient. More specifically, the changing magnetic fields can induce changes in fasciculation potentials or spontaneous motor unit potentials (sMUPs) in focused cortical or subcortical locations in the brain. Such changes can, in certain instances, provide therapeutic or other beneficial effects.

The apparatus can be used for targeted therapies, assisting in diagnosis, mapping out brain function for use in neuroscience research; non-medical applications of the apparatus can include stimulating areas of the brain to improve learning, concentration and education. As defined herein, medical applications can be considered treatments for a subject with a known or possible disease, condition, handicap, or other "sub-normal" attribute, while non-medical applications can include those in which the subject may or may not have or be diagnosed with any such conditions or attributes, but wishes to test or improve mental functioning in some manner. Non-medical applications can improve physical function as well, including such characteristics as coordination, speed, and stamina. It should be understood that for some subjects and in some instances, for example, with respect to subjects having very slight or imagined conditions or handicaps, this distinction can be blurred.

Medical applications include, but are not limited to, Tic Disorders and Tourette Syndrome, Parkinson's disease and other movement disorders such as Dystonia, Tremor and Ataxia, motor neurone diseases such as amyotrophic lateral sclerosis and multiple sclerosis, epilepsy, migraine and other headaches, complex regional pain syndrome (CRPS), neuropathy and fibromyalgia, tinnitus, stroke, psychological disorders including major depressive disorder and treatment resistant depression, anxiety disorders, obsessive compulsive disorder, eating disorders such as anorexia and bulimia, post-traumatic stress disorder (PTSD), psychiatric disorders including schizophrenia and bipolar disorder; visual, auditory and other hallucinations secondary to psychiatric disorders, attention disorders such as ADHD, substance abuse and addictions, learning disorders such as dyslexia and dysgraphia; speech disorders such as stuttering, memory disorders, dementia including Alzheimer's disease, traumatic brain injury, autism spectrum disorder, disorders of consciousness, and urinary incontinence. Recent studies have shown that TRPMS can be used for oncological therapy due to the effect that the rapidly changing magnetic fields have upon mitochondrial oxidation. In addition, magnetic fields are known to affect the position and alignment of polar molecules. Since cellular processes such as cell division utilize the properties of polar molecules, application of magnetic fields can disrupt or otherwise affect these processes. For example, cell division relies upon a particular positioning and alignment of polar septin and tubulin molecules. Use of convergent magnetic fields can thereby be used to affect cell division in target regions. In oncological treatments, the disrupting of cell division can possibly slow down tumor growth.

Non-medical applications include, but are not limited to, improvement or other modulation of: mood; attention and focus; motor and cognitive functions; anxiety such as social shyness; depression; memory and learning; smoking cessation, alcoholism and other addiction; and PTSD. Further non-medical applications include training and improvement of physical abilities and skills such as coordination and speed. This is made possible by the close connection between biological motor activity and electrical stimulation.

While the apparatus above is configured to conform to a patient's cranium and to apply magnetic fields into the patient's brain, similar configurations of magnetic assemblies and mounts can be placed on other portions of the anatomy to induce electric fields in tissues therein. For example, the magnetic assemblies and mounts can be fitted securely on straps, or other features that can cover appendages, gastrointestinal areas, the thorax (lungs, heart) and spinal areas. These areas can also be treated for medical or non-medical purposes using the magnetic assemblies.

In one exemplary configuration of the magnetic assembly device, the actuator device 302 may comprise both a motor for rotating the magnet and a lateral movement device (not shown) for changing the position of the magnet relative to the subject, such as solenoid. In this exemplary configuration, the lateral movement device in the magnetic assembly device can position the magnet closer or further away from brain of the subject. Whether and when there is lateral movement can be dependent upon particular treatment parameters that a user is applying to the subject. The lateral movement device optionally enables azimuth adjustment in addition to or as the lateral movement itself.

The magnetic assembly device 212 also includes one or more sensors 306 that can be used to monitor the magnetic field, the temperature of the assembly device, the current induced in the brain, or other data points regarding the assembly or the subject. Such data can comprise biophysical data as is known to those of skill in the art. In one arrangement, the sensors 306 comprise an array of one or more electrodes that are configured to measure electrical activity of the brain and to send the measured data as electrical signals back to the controller 232. The data gathered can be packaged, if desired, and uploaded to a persistent data store, which may be local or remote to the control device, e.g., to serve as supporting data with regard to the safety or efficacy of a particular treatment protocol unit or treatment protocol. Additionally, magnetic assembly device 212 includes an identification element, such as an RFID or QR tag and/or a memory unit (chip or card) that uniquely identifies each device. The memory unit is coupled to a standard port to allow the memory unit to be read externally. In some embodiments, the tag can be placed on the outer housing of the device or other accessible location. In other embodiments, the memory unit can be read by the controller 232 in order to determine the identifier of the magnetic assembly device.

Returning to FIG. 2, the controller 232 communicates with one or more of the magnetic assembly devices 212, 214, 216, 218 through a wired or wireless link or combinations thereof. The controller 232 communicates with the magnetic assembly devices using separately controllable communication links, one for each magnetic assembly device e.g., 212, 214. In addition, in some embodiments, the controller 232 can receive electrical signals from the attachment points e.g., 211, 213, 215, 217 whenever the magnetic assembly devices are being deployed. In certain configurations, however, the controller 232 can communicate with the magnetic assembly devices through the use of various combinations of one or more conduits, USB, serial, or wired or wireless communication links that are known to those of ordinary skill in the art.

Figure 3B:
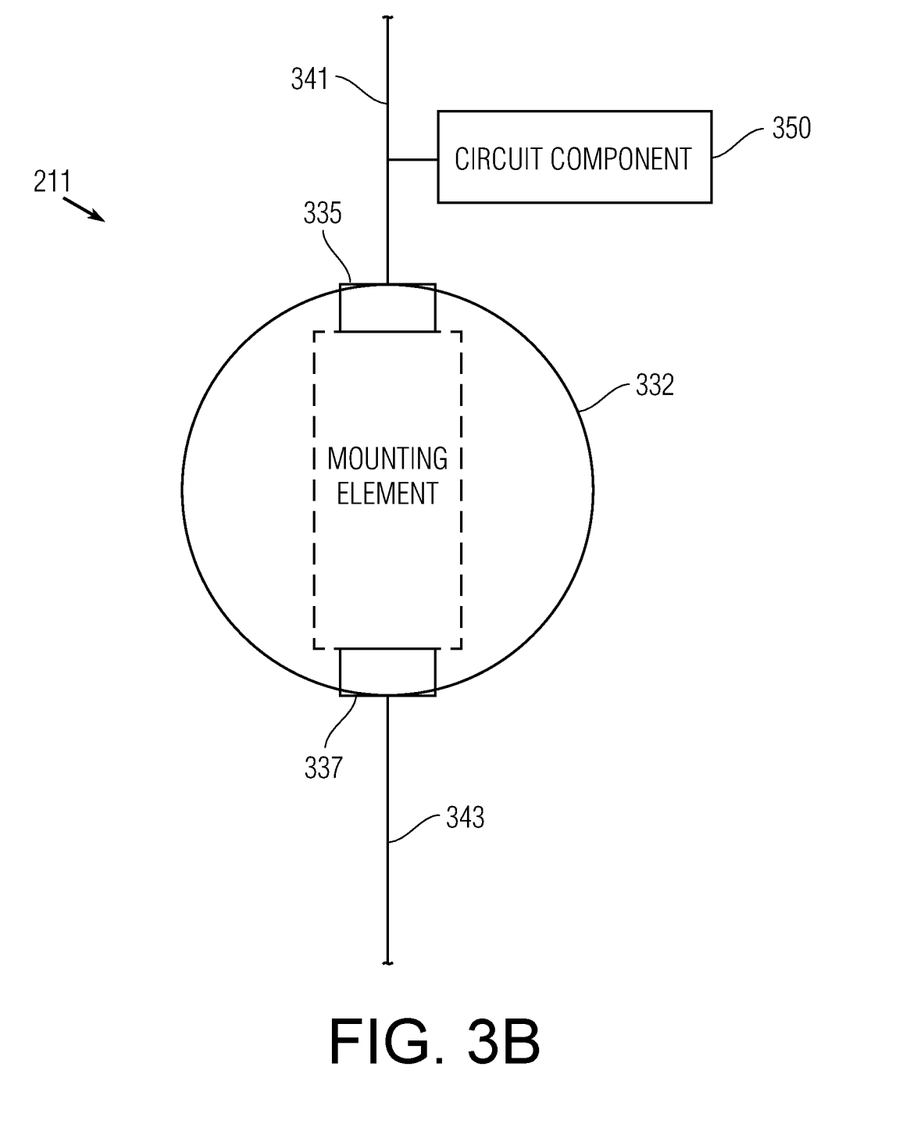
FIG. 3B is a schematic block diagram of an attachment point of a head mount according to an embodiment of the present invention.

FIG. 3B illustrates an exemplary embodiment of an attachment point 211 that can be used in the context of the present invention. Attachment point 211 includes an opening 332 in which a mounting element of a magnetic assembly device can be received (an example mounting element is shown in outline). Electrical contacts 335, 337 can be disposed at opposite edges of opening 332, as shown. A first electrical lead 341 is coupled to electrical contact 335, and a second electrical lead 343 is coupled to electrical contact 337. The controller 232 is coupled to the electrical leads 341, 343. A circuit component 350, which can be a resistor, capacitor, or inductive element, is coupled to electrical lead 341 and has a second coupling to cause the component to either be in parallel or in series with any particular mounted magnitude assembly device. When the mounting element of a magnetic assembly device is mounted into the opening, the mounting element, which is conductive, effectively closes the circuit by allowing current to flow in the channel between the contacts 335, 337 and the electrical leads 341, 343. In addition, when the magnetic assembly device is mounted, and the circuit is closed, a current or voltage signal flowing is modified by the circuit component 350 which is arranged either in parallel with the channel through the attachment point or in series, depending on the particular implementation. The properties of the circuit (e.g., resistance, impedance, capacitance, reactance) component 350 are chosen to be unique to the attachment point. Accordingly, the magnitude, phase, or both magnitude and phase of the modification of the current/voltage signal by the component of attachment point 211 is different from the magnitude or phase of the modification of all the other attachment point in the apparatus, which include circuit components with different characteristics. In this manner, each attachment point provides a unique current/voltage signature allowing the controller 232 to monitor each attachment point, and to determine when a magnetic assembly device has been mounted into any of the attachment points.

Returning again to FIG. 2, the controller 232 may comprise ports, drivers, gate arrays, logic switches or other devices configurable to selectively energize one or more magnet assembly devices 212, 214, 216, 218 in response to an instruction set or command signal from a processor 234 of the control device 230 and to receive electrical signals therefrom and from attachment points 211, 213, 215, 217. In one implementation, the controller 232 and processor 234 are part of a single computing device. In other implementations, the controller 232 and processor 234 can be housed in separate devices that are electrically connected.

The control device 230 can be a desktop or workstation class computer that executes a commercially available operating system, e.g., MICROSOFT WINDOWS, APPLE OSX, UNIX or Linux based operating system implementations. In accordance with further embodiments, the control device 230 can be a portable computing device such as a smartphone, wearable or tablet class device. For example, the control device 230 can be an APPLE IPAD/IPHONE mobile device, ANDROID mobile device or other commercially available mobile electronic device configured to carry out the processes described herein. In other embodiments, the control device 230 comprises custom or non-standard hardware configurations. For instance, the control device 230 can comprise one or more micro-computer(s) operating alone or in concert within a collection of such devices, network adaptors and interfaces(s) operating in a distributed, but cooperative, manner, or array of other micro-computing elements, computer-on-chip(s), prototyping devices, "hobby" computing elements, home entertainment consoles and/or other hardware.

The control device 230 can be equipped with a persistent memory device 236 that is operative to store the operating system in addition to one or more of software modules, such as those described herein to implement transcranial magnetic stimulation in accordance with embodiments of the present invention. In one embodiment of the present invention, the modules utilized by the control device 230 comprise software program code and data that are executed or otherwise used by the processor 234, thereby causing the control device 230 to perform various actions dictated by the software code of the various modules. The control device can also be in communication with a persistent data store that is located remotely and is accessible over a computer network via a network interface 238, which implements communication frameworks and protocols that are well known to those of skill in the art.

In certain embodiments, the persistent memory device 236 contains transcranial magnetic stimulation application program code 242. The control device also includes a library of treatment protocol units 240 for execution by the processor 234 in governing the operational parameters of the magnetic assembly devices. The treatment protocol units (TPUs) are, in one arrangement, data objects detailing specific operational characteristics that are implementable by the magnetic assembly devices. As is described in greater detail herein, one or more TPUs may be sequentially combined to form a treatment protocol. TPUs can be created locally or downloaded through the interface 238 from a remote site.

The operational parameters of a given TPU comprise a series of key-value pairs that users can define and which control operation of one or more magnetic assembly devices. More generally, a treatment protocol unit defines the manner in which one (and more typically at least two) or more magnetic assembly devices are activated to create electric fields across various areas of the brain of a subject over a window of time. Such information is used by the transcranial magnetic stimulation application program code to instruct the processor as to the manner in which to energize, via the controller, the set of magnetic assembly devices to create such a field. The one or more TPUs include instructions to the controller for generating signals that cause individual magnetic assembly devices to rotate. Receipt of such signals from the controller by a given magnetic assembly device causes its actuator to rotate its associated magnet at a particular frequency for a particular duration. Such rotation of the magnet at a set frequency results in the generation of a desired electric field within the brain, which may be used as part of a therapy, diagnosis, mapping or other treatment.

Advantageously, the transcranial magnetic stimulation application program code allows the user to select sets of treatment protocol units (TPUs) from library 240 to form one or more treatment protocols. The TPUs can be considered as "units of stimulation" that can be combined to implement specific treatments, referred to collectively as treatment protocols. A user interface can be provided by the transcranial magnetic stimulation application program code, for example a graphical user interface (GUI) or a text-based interface. Through the user interface, the user can define a set of TPUs that the processor applies to the subject as a set treatment protocol or can select a preset protocol comprising a set of TPUs defined locally or otherwise provided to the controller 232 from a remote site. As one example, in a neurological medical facility, a doctor or other medical professional can treat a patient with Parkinson's disease by selecting a treatment protocol from the TPU library 240 tailored for this condition.

According to one embodiment, the transcranial magnetic stimulation application program code serially applies the TPUs comprising a treatment protocol (e.g, like a script). Alternatively, the transcranial magnetic stimulation application program code may dynamically arrange and apply the treatment protocol units comprising a given treatment protocol. Still further, the processor may execute and apply certain treat protocol units in parallel, e.g., at the same time. The user may also share treatment protocols and TPUs with other users on other control devices by way of a network that the control device accesses via its network interface, which may further comprise receiving the individual treatment protocol units comprising a received treatment protocol.

In one particular arrangement, the transcranial magnetic stimulation application program code instructs the processor 234 of the control device 230 to apply a treatment that utilizes one or more particular magnetic assembly devices. The transcranial magnetic stimulation application program code can instruct the processor 234 to control the energization of all, or a portion of the magnetic assembly devices positioned on the transcranial system. An exemplary treatment protocol can involve a specific pattern of TPUs, the application of which is directed to the magnetic assembly device positioned in proximity to one or more areas of the subject's brain, such as the Broca's Area. The processor executing the transcranial magnetic stimulation application program code can generate a single control signal for distribution by the controller that details the desired rotation frequencies, durations, quiescent periods or other conditions for each of the magnetic assemblies. In other words, the user can select a treatment protocol and cause the system to implement a treatment or other procedure by implementing the pattern of treatment protocol units, in parallel or serial, all based on the selection of a particular treatment protocol.

A TPU can be represented as a data object which serves to provide structure to a set of data regarding a treatment protocol, such as but not limited to, rotation frequency, motor energization duration, quiescent period and specific energizing of a particular set of zero or more magnetic assembly devices. The TPU is processed by the TMS application code 242 to establish the drive or quiescent settings for each magnetic assembly device. TPUs can include a frequency value representing a rotational frequency for one or more magnetic assembly devices, a rotational duration, a placement area for application of the treatment protocol unit and a quiescent period, as example properties. TPUs can also implement a Theta Burst Stimulation (TBS) protocol. Here, the TBS protocol is defined as one or more active TPUs followed by a second, quiescent TPU. In one particular example, the active TPU(s) defines a three (3) pulse pattern delivered at a frequency of 50 Hz, each pulse lasting 20 ms. A quiescent TPU lasting 160 ms defines an inter-burst interval from the last burst of the present pattern to the first burst of the next pattern. The active and quiescent TPSs combine for a repeating treatment pattern of having a duration of 200 milliseconds. While a single TPU can define a multiple burst pattern, it is also envisioned that the active TPUs defines a single burst. Thus, a collection of single burst TPUs (each without a period of quiescence following the burst) followed by a single or collection of quiescent TPUs can also be used to define a TBS protocol.

In one or more implementations, execution of a particular TPU in a treatment protocol can cause issuance of a command to a single magnetic assembly device for treating a localized area. Similarly, a given treatment protocol unit may identify a set of one or more magnetic assembly devices on the basis of the location(s) of such magnetic device assembly on the head mount which energize for rotation over a period of time on the basis of the instructions in the given treatment protocol unit that the processor at the control device interprets. In another arrangement, magnetic assembly devices can be addressable on the basis of its connection point to the head mount, with the location of the magnetic device assembly being defined as a result of its connection to the head mount by virtue of the attachment points. As a related matter, signal feedback concerning the operational capabilities/status of the magnetic assembly devices that are attached to the head mount and their attachment points can coordinate with the system so as to permit treatment protocols to be selected, and to inform the clinician or other treatment provider, patient or other user that additional or different magnetic assembly devices have to be attached, and where they have to be attached, before a particular treatment protocol is initiated.

As noted previously, a given TPU identifies one or more particular key-value pairs that ultimately instruct the operational state of a magnetic assembly device at a given point in time. Accordingly, a given TPU need not define each key-value pair contained within a given treatment protocol unit, e.g., some keys can have a null or empty value. For example, a TPU can provide information about a quiescent period free of any energization state information, e.g., frequency and duration values are set to null. In such a configuration, a quiescence-only TPU operates as a break or spacer in the active sessions of a treatment protocol. In this way, quiescent periods can be introduced to accompany treatment protocol units lacking a quiescent period. By way of example, treatment protocol units that only define a quiescent period can be used to ensure that there is a set repetition frequency of between 0.1 to 2 Hertz.

A treatment for a particular condition can be implemented as a group of TPUs. According to one embodiment, the transcranial magnetic stimulation application program code instructs the processor to configure or assemble a set of TPUs according to an overall desired length of treatment. For example, if the desired treatment is two minutes, the transcranial magnetic stimulation application program code instructs the processor to assemble the TPUs into a treatment protocol is of the desired length, such as by looping the TPUs that comprise the treatment protocol until the treatment duration has been achieved. Alternatively, longer duration TPUs can be used in a given treatment protocol to provide a treatment program of a desired length. The resulting treatment protocol is a data object containing data used to instruct all or a portion of the magnetic assembly devices to generate a specific series of electric fields within the brain of the subject. Where different magnetic assembly devices mounted to the same cap 205 have different treatment protocol units applied, a treatment program dataset is created, which may be saved in a persistent data store as a library of treatment protocols. Thus, a collection of treatment protocols can be generated whereby different individual treatment protocols are used to control one or more specific magnetic assembly devices at any given time.

As described throughout, the processor at the control device executes the transcranial magnetic stimulation program code to variably energize one or more magnetic assembly devices spaced on the head mount 102 at locations that span at least a portion of the cranium of a subject. The control device provides functionality for user selection of one or more treatment protocols through interaction with the interface that the processor presents on a display device. The control device 230 may provide access to treatment protocols from local storage, as well as treatment protocols on remote data stores. According to one embodiment, the control device accesses a remote data store via a network through use of the network interface 238. Upon connection to the remote data store, the control device copies the transaction protocol to local storage for execution by the processor. Alternatively, the control device accesses the remote data store and reads transaction protocol information as needed, e.g., remote execution of the data.

The user can be presented with a listing of available treatment protocols, which may also comprise a listing of the individual treatment protocol units making up a given treatment protocol. Selection of a given treatment protocol can be made on the basis of applying a treatment directed towards a particular ailment. For example, a drop down menu can be provided in one embodiment by a graphical user interface that can list i) a set of exemplary potential ailments that require treatment, e.g.: depression, neurological and psychiatric disorders, migraines, aphasia, anxiety, Parkinson's disease, tinnitus, autism, schizophrenia, Alzheimer's, ALS, stroke (e.g. ischemic), Myotonic Dystrophy type 1 (DM1), stuttering, epilepsy, Parkinson's disease, oncological diseases including but not limited to glioblastoma, pain and dystonia, cocaine, opioid and other addictive behaviors; ii) non-medical stimulation treatments such as for improved concentration, short and long-term memory, learning, foreign language training, etc. A user can select a treatment protocol (comprising one or more treatment protocol units) that has been previously designed by another user, and possibly already verified by peers, to ameliorate such conditions, or provide such stimulus treatments. Alternatively, the user is free to select one or more treatment protocol units depending on specific conditions or circumstances, for example, one or more collections of treatment protocol units may be presented as having applicability to a particular ailment, such as addiction or pain. The data store that maintains the treatment protocols and/or treatment protocol units can by associated with metadata that functions as a suggestion as to the applicability of a given treatment protocol unit or treatment protocol.

Optionally, information can be received from a database over the network interface which can define (e.g., constrain) the selection of treatment protocols to those that correspond to a prescription by a clinician or other treatment provider. Optionally, the set of treatment protocols available for selection can be defined (e.g., constrained) as a function of prior treatments. For instance, a treatment protocol can comprise a regimen of treatments in which the duration, energy, or other parameters are established for a patient or other user, yet which vary over the course of treatment. In this way, a predefined regimen of treatment can be implemented (and repeated with the same or other subjects) with precision by virtue of providing a series of treatment protocols through a predefined regimen.

During operation, the processor executes transcranial magnetic stimulation program code 242 and retrieves TPUs from library 240 for execution in series or in parallel. Upon execution of the TPUs, the processor issues instructions to the controller to activate (or deactivate as the case may be) specific magnetic assembly devices which causes the motor or other actuator within a given magnetic assembly device to energize and induce the desired electrical fields within the brain of the wearer or to de-energize, as the case may be.

Per the discussion of transcranial magnetic stimulation using treatment protocols above, it can be appreciated that the proper functioning of each of the actuated magnetic assembly devices is crucial in order to deliver treatments as intended. To ensure that the transcranial magnetic stimulation apparatus performs properly on a regular basis, the providers of the magnetic assembly devices can stipulate limitations on the use of the devices by licensed use restrictions. For example, a magnetic assembly device can be licensed for a particular treatment protocol, for example, for treating Parkinson's disease, and the device can be licensed for a threshold number of uses under the license. For example, an assembly licensed for a Parkinson's treatment protocol can be limited to 20 uses. While a centralized permission server can be used to ensure that the magnetic assembly devices are used only under the licensed restrictions, this solution requires connectivity with a permission server at every instance in which a magnetic assembly is used during a treatment. To avoid this dependence on connectivity with a central authorizing entity, one embodiment of the invention uses a blockchain methodology to manage, monitor and control the usage of the magnetic assembly devices to ensure only licensed devices are used, and that the licensed devices are used for only the permitted number of licensed treatments.

Convergent Stimulation

Figure 4:
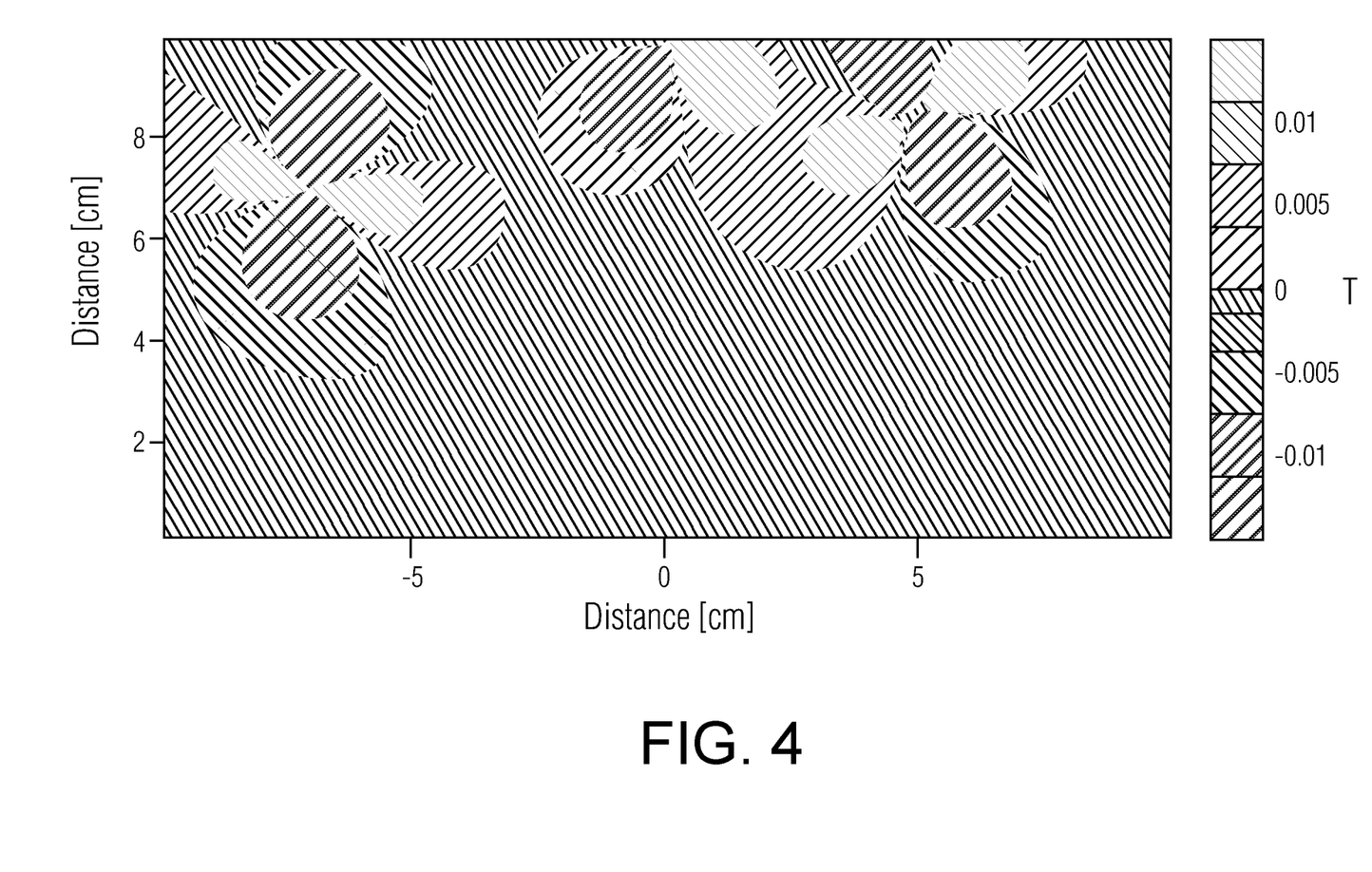
FIG. 4 is a schematic illustration showing magnetic fields produced by three magnets and the penetration of the fields in the brain of the patient.

Certain TPUs intended to treat particular conditions can target subcortical brain locations. As it is known that magnetic flux and induced voltage magnitude drop quickly with depth (proportional to $1/r^3$) special care is taken to ensure that the induced voltage generated at the location is sufficient to provide neurostimulation. The strength of the magnetic flux provided by an individual magnetic assembly is determined by the size of the magnet, the strength of the magnetic material and the rotational speed at which the magnet is rotated. For neurostimulation, additional factors including the neuronal environment and physiology also come into play. The equation for determining flux density B(t) at the targeted simulation site is modeled as a superposition of magnetic dipole fields as follows:

$$B(t) = \frac{\mu_0}{4\pi} \Sigma \left( \frac{3r_i(m_i(t) \cdot r_i}{r_i^5} - \frac{m_i(t)}{r_i^3} \right) \quad (1)$$

in which $m_i(t)$ is the magnetic moment of magnet (i) and $r_i$ is the distance between the center of the magnet and the targeted stimulation site. FIG. 4 is a schematic illustration showing magnetic fields produced by three magnets and the penetration of the fields in the brain of the patient. The distance between a first magnet and the stimulation site is $r_1$, the distance between a second magnet and the stimulation site is $r_2$, and the distance between a third magnet and the stimulation site is $r_3$. The resultant magnetic flux B(t) at the stimulation site is the sum of the magnetic field produced by each of the three magnets according to equation (1) above. If the magnets themselves are identical, the distances $r_1$, $r_2$, $r_3$ determine the magnitude of the magnetic flux at the stimulation site.

However, it is not the magnetic flux B(t) that is the determining factor for neuronal stimulation but rather it is the induced electric field at the stimulation site U(t). The induced voltage in a surrounding area A is calculated as follows:

$$U(t) = -\int \frac{dB(t)}{dt} \cdot dA \quad (2)$$

Figure 5:
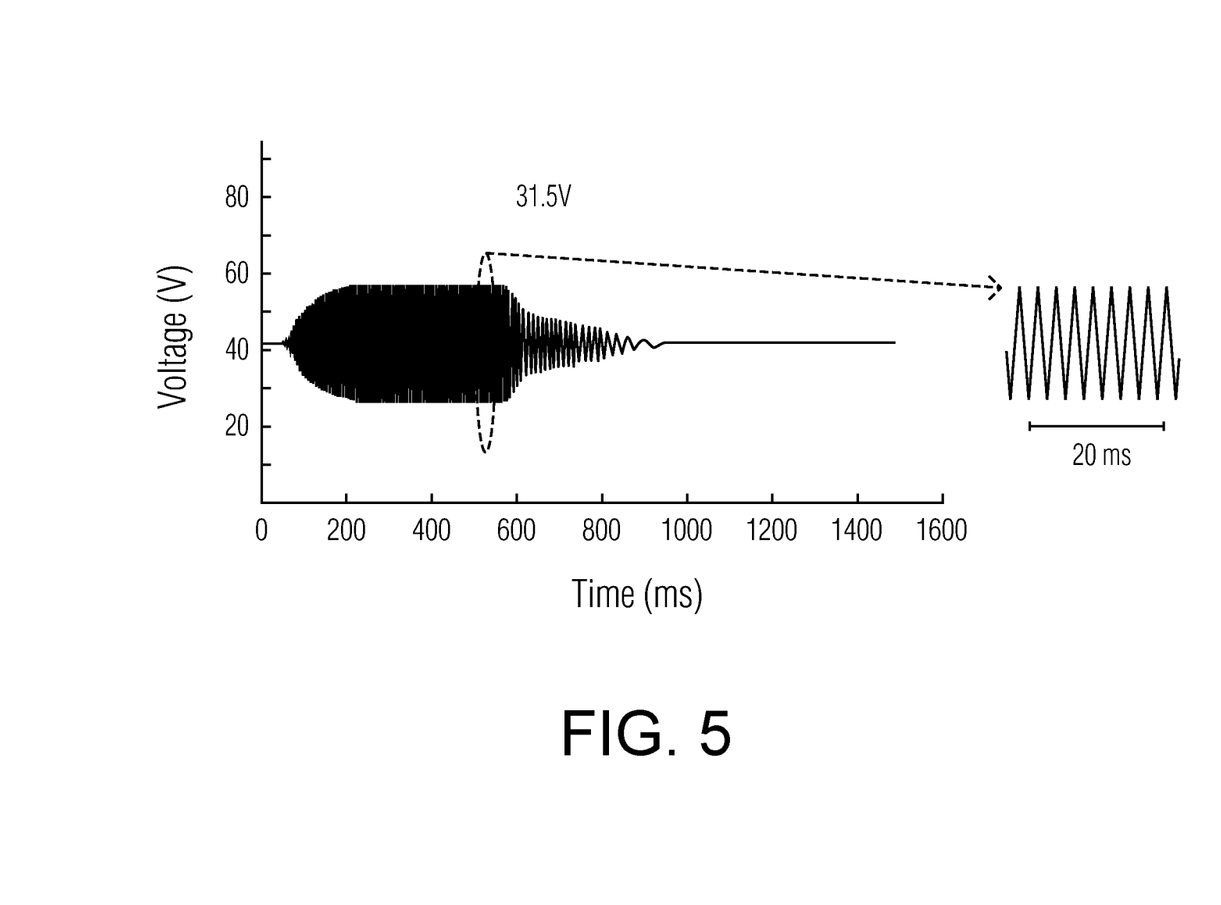
FIG. 5 is a graph showing an example of an oscillatory waveform of voltages induced by TRPMS magnets at a stimulation site.

From the dB(t)/dt term, the induced voltage is proportional to rate of change of the magnetic flux, which is in turn proportional to the rotational speed (frequencies) of the permanent magnets. Therefore, increasing the rotation rate of the magnets is one way to provide higher induced voltage using the same magnet size and type. FIG. 5 is a graph showing an example of voltages induced by TRPMS magnets at a stimulation site. The TRPMS stimulation is an oscillation that rises and falls in amplitude and frequency, and plateaus at a peak amplitude and frequency in between. The amplitude varies with magnet-to-simulation site distance, but the duration of the responses and frequency of the induced voltage oscillations do not change with distance. The amplitude of the inducted voltage signal reaches a stable peak in 75-150 ms.

Figure 6A:
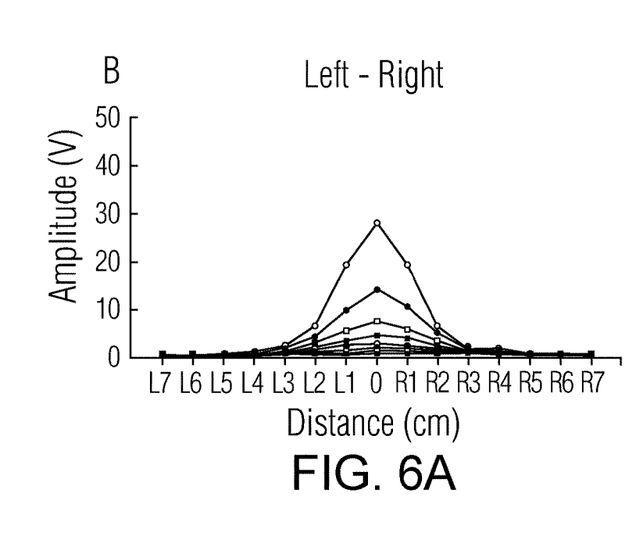
FIGS. 6A and 6B are graphs of induced electric field versus distance in the X plane (FIG. 6A) and Y plane (FIG. 6B).
Figure 6B:
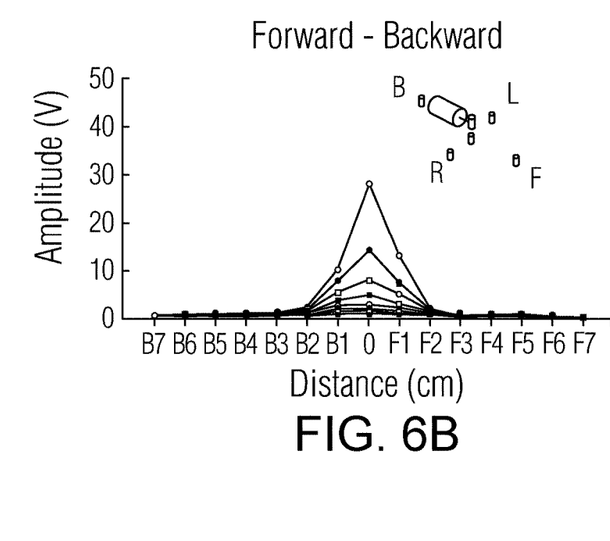

One of the advantages of TRPMS in comparison with TMS (which uses electromagnetic coils) is that the spatial spread of the voltage inducted by a plurality of TRPMS magnets is narrow in the X-Y plane (perpendicular to the depth(z) direction). The narrow spatial spread of the induced voltage enables focused stimulation of localized brain regions. This is shown in FIGS. 6A and 6B which are graphs showing induced voltages at different depths along the left-right (X) direction (FIG. 6A) and backward-forward (Y) direction, respectively. As the graphs indicate, the voltages induced by TRPMS fall to negligible levels 2 centimeters away from the central focus of stimulation.

Figure 7:
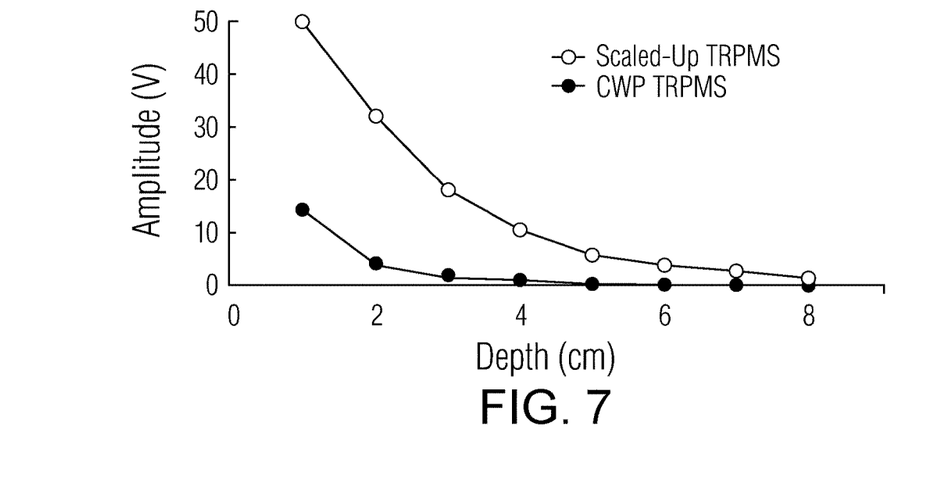
FIG. 7 is graph of induced electric field verse depth at low scaling and high scaling.

While TRPMS typically does not provide as much amplitude at depth as TMS, high induced voltages at depth can be obtained by a) focusing the magnetic flux generated by plurality of magnetic fields on the same location to combine the effects of multiple magnets and/or b) scaling up the power of each magnet, by increasing the size and/or strength of the magnets. FIG. 7 is a graph indicating how high induced voltages can be achieved at depth through the latter method of scaling up the power of the magnets. In the data shown in FIG. 7, the upper curve 400 represents data from larger rotating permanent magnets that would be less convenient to mount but nevertheless show that an 8-fold increase in induced voltage at depths of as high as 4-5 cm can be achieved using permanent magnets. Mountable versions of the magnetic assemblies can be implemented by using extra high-strength magnets to avoid unduly increasing the size of the magnets and to retain the utility of having these mounted on a cap that rests on the person's head or on a device that is otherwise positioned to be in contact with the person using it.

More generally, the strategy of combining the effects of multiple co-focused permanent magnets acting in concert on a localized brain region enables the use of regular (smaller) sized magnetic assemblies that can be conveniently coupled to a head mount. In certain implementations in which brain regions at high depths (>6 cm) are targeted for treatment, a combined strategy can be used. That is, small-sized magnets used in the magnetic assemblies on a head mount can be constructed with extra high strength materials, or regular-strength small-sized magnets can be combined with one or more larger sized magnets that can be coupled to the head mount according to specific requirements of the treatment.

Figure 8A:
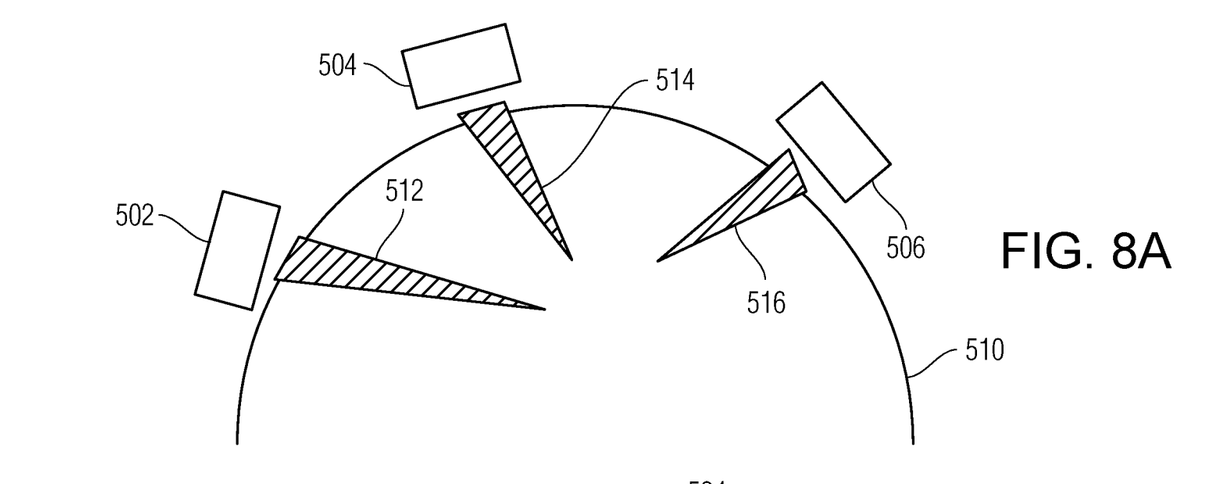
FIG. 8A is a schematic cross-sectional view of magnetic assemblies positioned on the skull of patient delivering non-convergent neurostimulation.
Figure 8B:
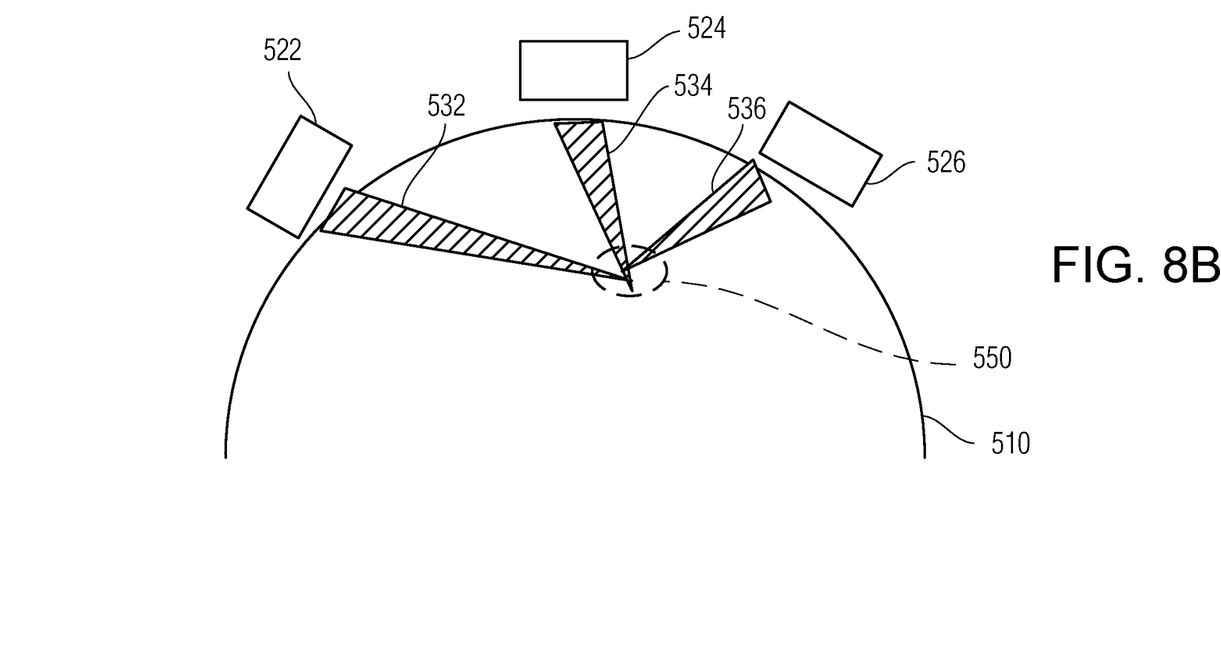
FIG. 8B is a schematic cross-sectional view of magnetic assemblies positioned on the skull of patient delivering convergent neurostimulation by additive induction of electric fields at subcortical depth.

In accordance with a salient aspect of this disclosure, the induced voltages used for a number of the treatments discussed above can be maintained below the level required to stimulate skeletal muscular movement, referred to as motor-evoked potentials (MEPs). Rather, it is found that induced electric fields in the ~12-30 V/m change, which are considerably below the MEP level, are sufficient to induce a significant increase in the frequency of spontaneously occurring fasciculation potentials or sMUPs. Such neurological activity has also been shown to be associated with therapeutic and other benefits across a range of conditions. FIGS. 8A and 8B provide a schematic illustration of the capability of magnetic assemblies of the present disclosure acting in concert to produce a convergent field. In FIG. 8A, magnetic assemblies with rotating permanent magnets 502, 504, 506 are positioned on the skull 510 of patient and each generate a magnetic field sufficient to induce voltages in the brain of a patient. The magnetic field generated by magnetic assembly 502 induces an envelope of electric field in a localized region of the patient's brain labeled 512. Similarly, the magnetic field generated by magnetic assembly 504 induces an envelope of electric field in area 514, and magnetic assembly 506 induces and envelope of electric field above the threshold in brain area 516. As shown, the envelopes 512, 514, 516 taper with depth in the brain, indicating that the induced electric field at depth decreases. In addition, the envelopes 512, 514 and 516 are distinct and do not overlap.

At a certain depth, the magnitude of the induced field generated by any single magnet might not be sufficient to generate SMUPs or other neuronal activity sufficient (e.g., each might be <12 V/m) to achieve a desired response at a targeted depth. This is the case in the illustration of FIG. 8A in which the envelopes of induced electric field 512, 514 do not overlap and do not combine at a deep location in the brain of the patient. By contrast, in FIG. 8B, magnetic assemblies 522, 524, 526 are selectively positioned so that the respective envelopes of induced electric fields 532, 534, 536 that they generate in the patient's brain converge at a subcortical brain region 550 (shown by the dashed ellipse). As the induced electric fields are additive, the total electric field induced in region 550 can be greater than the threshold required to achieve stimulation of SMUPs, or other effective neuromodulation, and the total electric field can remain at a level which is insufficient to stimulate skeletal muscular movement (below the MEP potential).

The combined electric fields are set at a strength necessary to achieve an effect on brain structures in the overlapping region 550. It is also important, however, to set the field strengths so that the effect of the electric field in non-overlapping portions of envelopes 532, 534, 536 is insufficient to produce undesired effects in the respective non-overlapping regions. In other words, the electric field strength is set so that it is smaller, particularly at shallow regions along the pathways of the electric field within each envelope 532, 534, 536 toward the overlapping region 550, than the field strength in the overlapping region where the electric field of the envelopes converge and combine. Setting the electric field strength with this in mind avoids unintended stimulation of brain structures in brain regions outside of the overlapping region 550.

By positioning the magnetic assemblies in locations in which their respective magnetic fields can act in concert at a targeted cortical or subcortical brain location, effective neuromodulation useful for treating, improving or otherwise effecting a variety of neurobiological conditions is possible. The positions at which the magnetic assemblies are set will depend on the brain region targeted, the amount of induced voltage required, and the characteristics of the magnetic assemblies (e.g., orientation, size, magnetic material, spin rate), among other factors. In some implementations, the convergent magnetic fields can be delivered simultaneously. In other implementations, the magnetic fields can be delivered sequentially and still achieve a similar additive effect.

Localized stimulation or modulation can be increased, in some instances, by controlling the rotating magnetic assemblies to rotate at different rates. The superposition of electromagnetic signals of different frequency produces a difference signal with a lower frequency which can, in certain circumstances and in certain brain regions, have a more dramatic effect than higher frequency signals alone. The rotation rate of each of the magnetic assemblies can be controlled individually to produce such effects.

Recent research has shown that the induction of electric fields in the brain using TRPMS can have additional effects beyond neurostimulation. For example, cortical or subcortical induced electric fields can cause depolarization of mitochondrial membrane potentials (MMP) and alter mitochondrial oxidation in brain tissue. This alteration in oxidation appears to lead to disruption of mitochondrial networks and can ultimately cause apoptosis in tumor cells. Therefore, selective targeting of tumor cells using convergent magnetic fields from a plurality of rotating magnets shows promise as a useful non-invasive oncological treatment through this mitochondrial disruption pathway. Furthermore, as mitochondrial activity is crucial to almost all biological functioning, modulation of such function using convergent TRPMS has wide application and can affect a multitude of normal or pathological conditions.

More generally, the convergent induced electric fields in brain regions can be used to affect the behavior of polar molecules. As discussed, for example in "Magnetic Field Application and its Potential in Water and Wastewater Treatment Systems" by N. Saidi et al. (Separation and Purification Reviews (2014)), polar molecules are affected strongly by static magnetic fields and dynamic magnetic fields (through the influence of the induced electric field). Many vital cellular processes rely specifically on the polarity of functional molecules. As an important example, cell division is mediated by tubulin and septin proteins which are both polar molecules. In order for cell division to occur these proteins must be positioned and aligned in a specific way. The induction of electric fields by TPRMS in specific brain regions can be used to disrupt or interfere with the timing of such positioning and alignment of tubulin and septin proteins, and can thereby affect the rate and timing of cell division in targeted brain regions.

Since TRPMS can deliver highly focal stimuli that can be scaled and it provides a way of delivering imperceptible multifocal stimuli simultaneously, sequentially and in defined spatiotemporal patterns, the magnetic assemblies can be used in concert to provide convergent stimulation and can also be scaled up. The controller enables the stimulus parameters and sites of stimulation to be varied dynamically using real time feedback. In addition, the stimulation can effectively influence a variety of neuronal patterns and geometries because the magnetic field direction can sweep over a continuum of angles, depending on the configuration of the magnets.

While this specification contains many specific embodiment details, these should not be construed as limitations on the scope of any embodiment or of what can be claimed, but rather as descriptions of features that can be specific to particular embodiments of particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Publications and references to known registered marks representing various systems are cited throughout this application, the disclosures of which are incorporated herein by reference. Citation of any above publications or documents is not intended as an admission that any of the foregoing is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details may be made therein without departing from the spirit and scope of the invention. As such, the invention is not defined by the discussion that appears above, but rather is defined by the claims that follow, the respective features recited in those points, and by equivalents of such features.

What is claimed is:

1. A method of stimulating or biomagnetically affecting a biological, cellular or biochemical function or structure in a targeted subcortical location in a brain of a patient using a TRPMS (Transcranial Rotating Permanent Magnetic Stimulation) apparatus provided on a head mount, the apparatus having a plurality of releasable magnetic assemblies with rotating permanent magnets operable to rotate for controlled durations and spin rates, the method comprising:

positioning two or more of the plurality of magnetic assemblies on locations of the head mount selected to stimulate the targeted subcortical location in the brain of the patient; and     activating the plurality of magnetic assemblies at the selected locations to generate magnetic fluxes of a selected strength, frequency and duration directed into the brain of the patient, wherein the magnetic flux directed into the brain of the patient from each of the assemblies is operative to generate induced electric fields in regions of the brain;

wherein the regions of induced electric fields generated by each of the plurality of magnetic assemblies converge and overlap in the targeted subcortical location and combine to a magnitude sufficient to stimulate or affect the biological, cellular or biochemical function or structure in the targeted subcortical location, while the induced electric fields are insufficient to affect the biological, cellular or biochemical function or structure outside of the regions where the induced electric fields overlap;

wherein the targeted subcortical location is over 2 centimeters deep as measured from an external surface of the brain; and wherein the induced electric fields as combined at the targeted subcortical location has a magnitude in a range of 12 V/m to 30 V/m.

2. The method of claim 1, wherein the regions in which the induced electric fields are generated by each of the plurality of magnetic assemblies converge and overlap in the targeted subcortical location and combine to a magnitude sufficient to increase a frequency of spontaneously occurring fasciculation potentials (sMUPs) of neurons in the targeted subcortical location.

3. The method of claim 1, wherein the regions in which the induced electric fields are generated by each of the plurality of magnetic assemblies converge and overlap in the targeted subcortical location and combine to a magnitude sufficient to modulate mitochondrial activity in the targeted subcortical location.

4. The method of claim 3, wherein modulation of the mitochondrial activity in the targeted subcortical location causes apoptosis of oncological tumor cells in the targeted location.

5. The method of claim 1, wherein the regions in which the induced electric fields are generated by each of the plurality of magnetic assemblies converge and overlap in the targeted subcortical location and combine to a magnitude sufficient to modify a position or orientation of polar molecules involved in a cellular process in the targeted subcortical location.

6. The method of claim 5, wherein the regions in which the induced electric fields are generated by each of the plurality of magnetic assemblies converge and overlap in the targeted subcortical location and combine to a magnitude sufficient to modify a position or orientation of septin and tubulin molecules to regulate cell division in the targeted subcortical location.

7. The method of claim 1, wherein the neurons in the targeted location are stimulated to provide a treatment or therapy for a medical condition.

8. The method of claim 1, wherein the neurons in the targeted location are stimulated to modify neuronal activity for a non-medical purpose.

9. An apparatus for stimulating or biomagnetically effecting a biological, cellular or biochemical function or structure in a targeted subcortical location in a brain of a patient comprising:

a head mount positioned on the patient; and a plurality of releasable magnetic assemblies coupled to the head mount including rotating permanent magnets operable to rotate for controlled durations and spin rates, the plurality of magnetic assemblies being selectively positioned at locations of the head mount to stimulate the targeted subcortical location in the brain of the patient;

wherein activation of each of the plurality of magnetic assemblies at the selected locations directs magnetic fluxes of a selected strength, frequency and duration into the brain of the patient, wherein the magnetic flux directed into the brain of the patient from each of the assemblies is operative to generate induced electric fields in regions of the brain; and wherein the regions of induced electric fields generated by each of the plurality of magnetic assemblies converge and overlap in the targeted subcortical location and combine to a magnitude sufficient to stimulate or affect the biological, cellular or biochemical function or structure in the targeted subcortical location, while the induced electric fields are insufficient to affect the biological, cellular or biochemical function or structure outside of the regions where the induced electric fields overlap, and wherein the induced electric fields as combined at the targeted subcortical location has a magnitude in a range of 12 V/m to 30 V/m and the targeted subcortical location is over 2 centimeters deep as measured from an external surface of the brain.

10. The apparatus of claim 9, wherein the regions in which the induced electric fields are generated by each of the plurality of magnetic assemblies converge and overlap in the targeted subcortical location and combine to a magnitude sufficient to increase a frequency of spontaneously occurring fasciculation potentials (sMUPs) of neurons in the targeted subcortical location.

11. The apparatus of claim 10, wherein the neurons in the targeted location are stimulated to provide a treatment or therapy for a medical condition.

12. The apparatus of claim 10, wherein the neurons in the targeted location are stimulated to modify neuronal activity for a non-medical purpose.

13. The apparatus of claim 9, wherein the regions in which the induced electric fields are generated by each of the plurality of magnetic assemblies converge and overlap in the targeted subcortical location and combine to a magnitude sufficient to modulate mitochondrial activity in the targeted subcortical location.

14. The apparatus of claim 13, wherein modulation of the mitochondrial activity in the targeted subcortical location results in apoptosis of oncological tumor cells in the targeted location.

15. The apparatus of claim 9, wherein the regions in which the induced electric fields are generated by each of the plurality of magnetic assemblies converge and overlap in the targeted subcortical location and combine to a magnitude sufficient to modify a position or orientation of polar molecules involved in a cellular process in the targeted subcortical location.

* * * * *